United States Patent
Kimura et al.

[11] Patent Number: 5,451,510
[45] Date of Patent: Sep. 19, 1995

[54] PROCESS FOR PREPARING 3α, 7α-DIHYDROXY-12-KETO-5β-CHOLANIC ACID USING BACILLUS SPP. FERM BP-3394 AND FERM BP-3397

[75] Inventors: Hiromi Kimura, Koshigaya; Akio Okamura, Okegawa; Hiroshi Kawaide, Fujimi, all of Japan

[73] Assignee: Tokyo Tanabe Company, Limited, Tokyo, Japan

[21] Appl. No.: 964,192

[22] Filed: Oct. 21, 1992

[30] Foreign Application Priority Data

Oct. 24, 1991 [JP] Japan .................. 3-277799

[51] Int. Cl.$^6$ .......................... C12P 33/02; C12N 1/20
[52] U.S. Cl. .......................... 435/52; 435/61; 435/170; 435/252.5; 435/136
[58] Field of Search ............. 435/52, 61, 136, 170, 435/252.5

[56] References Cited

U.S. PATENT DOCUMENTS

| | | | |
|---|---|---|---|
| 2,236,574 | 4/1941 | Koester et al. | 435/61 |
| 2,341,110 | 2/1944 | Mamoli et al. | 435/61 |
| 2,905,592 | 9/1959 | Shull et al. | 435/61 |
| 2,992,973 | 7/1961 | Terumichi et al. | 435/61 |
| 3,037,913 | 6/1962 | Feldman et al. | 435/61 |
| 3,037,914 | 6/1962 | Feldman et al. | 435/61 |
| 3,623,954 | 11/1971 | Klesuch et al. | 435/61 |
| 3,801,460 | 4/1974 | Stoudt et al. | 435/52 |
| 4,546,078 | 10/1985 | Manecke et al. | 435/52 |

FOREIGN PATENT DOCUMENTS

| | | |
|---|---|---|
| 1-20873 | 1/1982 | Japan . |
| 2-62234 | 1/1982 | Japan . |
| 1-51998 | 12/1986 | Japan . |

Primary Examiner—David M. Naff
Assistant Examiner—L. Blaine Lankford
Attorney, Agent, or Firm—McGlew and Tuttle

[57] ABSTRACT

3-α, 7-α-dihydroxy-12-keto-5-β-cholanic acid is microbially produced from cholic acid by alkalophilic Bacillus strains. The preferred strains are Bacillus sp. FERM BP-3394 and Bacillus sp. FERM BP-3397.

4 Claims, No Drawings ns and a process for preparing 3α, 7α-dihydroxy-12-
PROCESS FOR PREPARING 3α, 7α-DIHYDROXY-12-KETO-5β-CHOLANIC ACID USING BACILLUS SPP. FERM BP-3394 AND FERM BP-3397

TECHNICAL FIELD OF THE INVENTION

The present invention relates to novel microorganisms and a process for preparing 3α, 7α-dihydroxy-12-keto-5β-cholanic acid (referred hereinafter as 12-keto-cholic acid), which is an intermediate of a preparation of chenodeoxycholic acid useful for a gallstone dissolving agent and for raw material for preparation of ursodeoxycholic acid, cholanopoietic, from 3α, 7α, 12α-trihydroxy-5β-cholanic acid (referred hereinafter as cholic acid) by the use of microorganisms.

BACKGROUND OF THE INVENTION

Up to the present, as a chemical process for preparing 12-keto-cholic acid from cholic acid, a process comprising selective oxidation of a hydroxyl group of 12-position of cholic acid is known. And as a microbiological process for preparing 12-keto-cholic acid from cholic acid, a process by the use of Micrococcus (Japanese Patent Publication No. Hei 1-51998), a process by the use of Arthrobacter (Japanese Patent Publication No. Hei 1-20873, Japanese Patent Publication No. Hei 2-62234), for example, are known.

But the former chemical process for preparing 12-keto-cholic acid has problems concerning reactivity, selectivity of the reaction and safety in operations, and the process is not satisfactory with regard to its yield and the purity of products. The latter process using microorganisms is not necessarily satisfactory because microorganisms essentially assimilate cholic acid substrate and produce some by-products, and with regards to the yield and the property of the products.

As the results of our researches of microorganisms having 12-keto-cholic acid productivity and of processes for preparing 12-keto-cholic acid by the use of said microorganisms, we have eventually found that a microorganism belonging to a genus of Bacillus which may grow in a high alkaline culture medium containing high concentration of cholic acid wherein usual microorganisms may not grow produces 12-keto-cholic acid, 3α, 12α-dihydroxy-7-keto-5β-cholanic acid and 3α-hydroxy-7,12-diketo-5β-cholanic acid as main converting products from cholic acid substrate, and we named the microorganism Bacillus sp. TTUR 2-2 (Fermentation Research Institute, Agency of Industrial Science and Technology (Japan) deposit No. 11861 (referred hereinafter as FERM1861)). This microorganism was isolated from the soil of Yonezawa city Yamagata prefecture.

Above bacterium has the ability to oxidize hydroxy groups of mainly 7-position and 12-position of cholic acid to keto groups and a hydroxy group of 3-position, though weak it is, of cholic acid to keto group, but has no ability to assimilate or decompose cholic acid.

Further as said bacterium can grow in the high alkaline medium, it is possible to prepare culture media containing high concentration of cholic acid, and Sterilization operation to the culture media prior to cultivation of bacteria, which operation is necessary for usual culture media, may be avoided.

We have attained the present invention through isolation of mutant strain having productivity of 12-keto-cholic acid from cholic acid with substantially 100% conversion and substantially 100% yield by means of mutation treatment such as irradiation of ultraviolet ray, X-ray, gamma-ray and so forth, or contact with mutagenesis agent such as N-methyl-N'-nitro-N-nitrosoguanidine (referred herein after as NTG), 4-nitroquinoline-N-oxide, acriflavin, ethyl methane sulfonate and so forth.

Therefore the present invention provides a process for preparing 12-keto-cholic acid comprising: cultivating a bacterium belonging to Bacillus having 12-keto-cholic acid productivity in a nutrition medium containing cholic acid, making the bacterium produce 12-keto-cholic acid in the culture medium and collecting 12-keto-cholic acid.

SUMMARY AND OBJECTS OF THE INVENTION

The primary object of the present invention is to provide a process for preparing 3α,7α-dihydroxy-12-keto-5β-cholanic acid comprising: cultivating microorganism having productivity of 3α, 7α-dihydroxy-12-keto-5β-cholanic acid belonging to the genus of Bacillus in a nutrient medium containing 3α, 7α, 12-trihydroxy-5β-cholanic acid, letting the microorganism produce 3α, 7α-dihydroxy-12-keto-5β-cholanic acid in the culture medium and collecting said acid.

Another object of the present invention is to provide bacteria which achieve productivity of 3α, 7α-dihydroxy-12-keto-5β-cholanic acid.

DETAILED DESCRIPTION OF THE INVENTION

We named above mutant strains originating Bacillus sp. TTUR 2-2 as Bacillus sp. TTUR 2-M4-124 (FERM3394) and Bacillus sp. TTUR 2-M4-336 (FERM3397). Methods for isolating said bacteria are as follows:

(1) Bacillus sp. TTUR 2-M4-124

A platinum loop amount of Bacillus sp. TTUR 2-2 cultivating in a slant of alkaline NA medium (composition: normal bouillon 'EIKEN' (trade name) 1.8%, agar 1.8%, sodium carbonate 0.75%, pH10) was inoculated into a test tube (30φ×190 mm) containing 20 ml of HORIKOSHI medium I (composition: glucose 1%, peptone 0.5%, yeast extract 0.5%, dipotassium hydrogen phosphate 0.1%, magnesium sulfate 7hydrates 0.02%, sodium carbonate 1%, pH10 ), and the bacterium was cultivated under shaking at 30° C. for 16 hours.

Then, above bacterium in logarithmic growth phase was collected aseptically by means of centrifugal separation, and was washed with 10 ml of 0.1M tris-maleic acid buffer(pH8.0) for three times. The bacterium after washing was added to 25 ml of the same buffer solution to form suspension, then NTG was added to the suspension so that the final concentration of the bacterium should be 60 μg/ml, and the bacterium in the suspension was incubated at 30° C. for 30 minutes and was subjected to a mutation treatment. The death rate of the Bacillus sp. TTUR 2-2 during said treatment was 85%.

Then taking up 1 ml of the suspension of the bacterium, diluting the suspension with 9 ml of 0.1M sodium carbonate buffer(pH9.5), collecting the bacterium by means of a centrifugal separator, and after washing with the same buffer for two times, the bacterium was suspended into 10 ml of alkaline NB medium (composition: normal bouillon 'EIKEN' 1.8%, sodium carbonate 0.75%, pH10 ). The bacterium suspension thus prepared was optionally diluted with alkaline NB medium, applied on the alkaline NA plating culture medium so that 10–100 colonies should appear, and cultivated at 30° C. for two days.

Among the colonies appeared, isolating a colony of middle size growing two days after the start of the cultivation, transplanting said colony to a slant of 5% CA agar medium (composition: a medium adding cholic acid 5%, sodium hydroxide 0.5%, agar 1.8% to the HORIKOSHI medium I, pH10), and the bacterium of the colony was cultivated for three days at the temperature of 30° C. Well grown strain was selected and a platinum loop amount of said strain was inoculated into a test tube (16.5$\phi \times$165 mm) containing 5% of CA liquid medium (composition: removing agar from 5% CA agar medium, pH10). The amount of medium in the test tube was 4 ml. The strain in the test tube was cultivated under shaking at 30° C. for three days. Products converted in the culture medium was investigated by means of thin layer chromatography and we have found mutant strain specifically producing 3$\alpha$-hydroxy-7,12-diketo-5$\beta$-cholanic acid, and the strain was named Bacillus sp. TTUR 2-M4 (FERM3393). Above process for obtaining mutant strain is referred hereinafter as NTG treatment.

Then the NTG treatment was repeated to the Bacillus sp. TTUR 2-M4 obtained by above NTG treatment as a parent strain on condition that 5% CA liquid medium was used for the medium for the first growing strain, and NTG concentration in the NTG treatment was 60 $\mu$g/ml. As a result, we found a strain specifically producing 12-keto-cholic acid and we named the strain as Bacillus sp. TTUR 2-M4-124. The death rate of Bacillus sp. TTUR 2-M4 during above operation was 15%.

(2) Bacillus sp. TTUR 2-M4-336

The NTG treatment was repeated to the Bacillus sp. TTUR 2-M4 obtained by above NTG treatment of (1) as a parent strain on condition that 5% CA liquid medium was used for the medium for the first growing, and NTG concentration in the NTG treatment was 100 $\mu$g/ml. As a result, we found a strain specifically producing 12-keto-cholic acid and we named the strain as Bacillus sp. TTUR 2-M4-336. The death rate of Bacillus sp. TTUR 2-M4 during above operation was 45%.

In this regard, it is to be noted that a deposit of Bacillus sp. TTUR 2-2 ( Deposit No. FERM P-11861 ) was made on Nov. 22, 1990 in the International Depository: Fermentation Research Institute, Agency of Industrial Science and Technology, 1-3, Higashi 1 chome Tsukuba-shi Ibarak-ken, 305 Japan; and that a deposit of each of Bacillus sp. TTUR 2-M4 (Deposit No. FERM BP-3393), Bacillus sp. TTUR 2-M4-124 (Deposit No FERM BP-3394) and Bacillus sp. TTUR 2-M4-336 (Deposit No. FERM BP-3397) was made on May 3, 1991 in said International Depository; all of said deposits having been made in accordance with the Budapest Treaty.

Bacteriological properties of said bacteria are listed in following tables 1 to 4. Methods for tests and classifications are according to the BERGEY's MANUAL OF Systematic Bacteriology, and if otherwise defined, to all media used herein sodium carbonate was added and all media was controlled pH 10.

TABLE 1

Morphology of various Bacillus sp. TTUR

| Bacillus sp. TTUR | TTUR 2-2 | TTUR 2-M4 | TTUR 2-M4-124 | TTUR 2-M4-336 |
|---|---|---|---|---|
| form | rod | rod | rod | rod |
| size ($\mu$m) | 0.4–0.7 $\times$ 1.5–4.5 | 0.4–0.7 $\times$ 1.5–4.5 | 0.4–0.7 $\times$ 1.5–4.5 | 0.4–0.7 $\times$ 1.5–4.5 |
| polymorphism | none (partially chained) | none (partially chained) | none (partially chained) | none (partially chained) |
| flagellum | peritrichous | peritrichous | peritrichous | peritrichous |
| spore site | near cell end | near cell end | near cell end | near cell end |
| sporangium | swells slightly | swells slightly | swells slightly | swells slightly |
| size ($\mu$m) | 0.3–0.7 $\times$ 0.6–1.2 | 0.3–0.7 $\times$ 0.6–1.2 | 0.3–0.7 $\times$ 0.6–1.2 | 0.3–0.7 $\times$ 0.6–1.2 |
| gram-stain | variable | variable | variable | variable |
| acid fastness | none | none | none | none |

TABLE 2

Growth of bacteria in various media
(TTUR 2-2, TTUR 2-M4, TTUR 2-M4-124 and TTUR 2-M4-336 show following growth conditions.)

| | growth condition | |
|---|---|---|
| type of medium | pH 7.0 | pH 10.0 |
| nutrient agar plate culture | poor | irregular, convex, auriculate or lobate; milky white and lustrous |
| nutrient agar slant culture | poor | grows in a spreading state cloth. no pigment formed |
| nutrient liquid culture | slightly grows | grows, slightly turbid sediment observed |
| gelatin stab culture | not liquefied due to insufficient growth | liquefied in stratiform |
| litmus milk | change hardly observed | grows and liquefying no litmus color change due to alkalinity |

TABLE 3

Physiological properties of TTUR 2-2, TTUR 2-M4, TTUR 2-M4-124 and TTUR 2-M4-336

| | |
|---|---|
| reduction of nitrate salts | none or very weak |
| denitrification reaction | unobserved |
| MR (methyl red) test | no change observed due to alkalinity of the medium |
| VP test | negative |
| indol formation | none |
| hydrogen sulfide formation | none |
| hydrolysis of starch | reactive |
| utilization of citric acid | |
| Kozer's medium | not utilized |
| Christensen's medium | utilized |
| inorganic nitrogen | |
| ammonium salts | scarcely utilized |
| nitrate salts | scarcely utilized |
| pigment formation | none |
| urease (pH 9) | negative |
| oxidase | positive |
| catalase | positive |
| growth range : pH: | pH 7–11 (optimum pH 9–10) |
| temp. | |
| (of 2-M4-124, 336) | 15–40° C. (optimum 30–37° C.) |
| (of TTUR 2-2, 2-M4) | 15–43° C. (optimum 30–37° C.) |
| attitude to oxygen | aerobic |
| O-F test | grows in aerobic condition, slightly forms acid, but not gas |
| sodium chloride resistance | grows in 10% sodium chloride, but not in 15% sodium chloride |

TABLE 4

| | | Acid and gas formation from various sugars (pH 9) | | | |
|---|---|---|---|---|---|
| sugar | production | TTUR 2-2 | TTUR 2-M4 | TTUR 2-M4-124 | TTUR 2-M4-336 |
| L-arabinose | acid | ± | ± | ± | − |
| | gas | − | − | − | − |
| D-xylose | acid | ± | − | ± | − |
| | gas | − | − | − | − |
| D-glucose | acid | ± | ± | ± | ± |
| | gas | − | − | − | − |
| D-mannose | acid | − | − | − | − |
| | gas | − | − | − | − |
| D-fructose | acid | + | + | + | + |
| | gas | − | − | − | − |
| D-galactose | acid | − | − | − | − |
| | gas | − | − | − | − |
| maltose | acid | + | + | + | + |
| | gas | − | − | − | − |
| sucrose | acid | + | + | ± | − |
| | gas | − | − | − | − |
| lactose | acid | − | − | − | − |
| | gas | − | − | − | − |
| trehalose | acid | + | + | ± | + |
| | gas | − | − | − | − |
| D-sorbit | acid | − | − | − | − |
| | gas | − | − | − | − |
| D-mannit | acid | + | + | + | + |
| | gas | − | − | − | − |
| D-inosit | acid | − | − | − | − |
| | gas | − | − | − | − |
| glycerol | acid | − | − | − | − |
| | gas | − | − | − | − |
| starch | acid | + | + | + | + |
| | gas | − | − | − | − |

According to the above observations, it is obvious that Bacillus sp. TTUR 2-2 is a microorganism belonging to the genus of Bacillus because Bacillus sp. TTUR 2-2 is a sporeforming and aerobic bacterium. But considering that optimum pH for growth exists alkaline side in the pH range of 9 to 10, Bacillus sp. TTUR 2-2 is not typical Bacillus microorganism.

And when comparing Bacillus sp. TTUR 2-2 with *Bacillus alcalophilus* and *Bacillus alcalophilus* subsp. halodurans known as standard alkalophilic bacteria in Bacillus, there are remarkable differences between them in the form and the periphery of the colony.

As alkalophilic strains having irregular shape of colony and lobate colony periphery, *Bacillus cereus* 8-1 (FERM 2885, Japanese Patent Publication No. Sho 53-13708) and Bacillus alcalophylus 202-1 (FERM 2674, Japanese Patent Publication No. Sho 53-27786) have been reported, but their colony forms are different from that of Bacillus sp. TTUR 2-2.

In table 5, Main characteristics of Bacillus sp. TTUR 2-2, Bacillus sp. TTUR 2-M4-124, Bacillus sp. TTUR 2-M4-336 and Bacillus alcalophilus are shown, and in table 6, main characteristics of *Bacillus alcalophilus* subsp. halodurans, *Bacillus cereus* 8-1 (FERM2885, Japanese Patent Publication No. Sho 53-13708) and Bacillus alcalophilus 202-1, (FERM 2674, Japanese Patent Publication No. Sho 53-27786 ), respectively, are shown.

TABLE 5

| | Main characteristics of bacteria (No. 1) | | | |
|---|---|---|---|---|
| Bacillus sp. | TTUR 2-2 | TTUR 2-M4-124 | TTUR 2-M4-336 | Bacillus alcalophilus |
| colony shape | irregular | irregular | irregular | circular |
| colony periphery | auriculate | auriculate | auriculate | entire |
| colony color | milky white | milky white | milky white | milky white |
| gelatin liq-uefactor | stratiform | stratiform | stratiform | stratiform |
| growth under anaerobic environment | − | − | − | − |
| growth temp. | 15–43° C. | 15–40° C. | 15–40° C. | up to 46° C. |
| optimum temp. | 30–37° C. | 30–37° C. | 30–37° C. | 33–35° C. |
| NaCl tolerance (15%) | − | − | − | − |
| utilization of ammonium salt | − | − | − | − |
| reduction of nitrate | − | − | − | − |
| utilization of citric acid (Kozer's) | − | − | − | − |
| acid formation from sugar | | | | |
| L-alabinose | ± | ± | − | + |
| D-xylose | ± | ± | ± | + |
| D-glucose | ± | ± | − | + |
| sucrose | + | ± | − | + |

TABLE 6

| | Main characteristics of bacteria (No. 2) | | |
|---|---|---|---|
| Bacillus | Bacillus alcalophilus subsp. halodurans | Bacillus cereus 8-1 (FERM 2885) | Bacillus alcalophilus 202-1 (FERM 2674) |
| colony shape | circular | irregular | irregular |
| colony periphery | entire | lobate | lobate |
| colony color | milky white | light yellow | milky white |
| gelatin liquefactor | crateri-form | | stratiform |
| growth under anaerobic environment | + | − | + |
| growth temp. | below 54° C. | below 45° C. | below 50° C. |
| optimum growth temp. | about 48° C. | 40–45° C. | 40–43° C. |
| NaCl tolerance (15%) | + | | |
| utilization of ammonium salt | | − | ± |
| reduction of nitrate | + | | |
| utilization of citric acid (Kozer's) | | ± | + |
| acid formation from sugar | | | |
| L-alabinose | + | + | + |
| D-xylose | + | + | + |
| D-glucose | + | + | + |
| sucrose | + | + | + |

It is reasonable to classify TTUR 2-2 as new species of bacterium because TTUR 2-2 is distinguishable from known species with respect to the bacteriological property, especially optimum pH range for growth is in alkaline side around 9 to 10, though TTUR 2-2 is sporeforming aerobic bacterium.

And as it is thought that mutant strains usually belong to the same species as its parent strain, we determined that the Bacillus TTUR 2-M4-124 and TTUR 2-M4-336 which being secondary mutants of Bacillus sp. 2-2 belong to the same species of bacteria as the parent strain.

Namely, bacteria of the present invention are not limited to Bacillus sp. TTUR 2-M4-124 and TTUR 2-M4-336, but any bacteria belonging to Bacillus and being able to produce 12-keto-cholic acid from cholic acid substrate may be used.

Culture media used in the present invention is any media in which above bacteria can grow, for example, as carbon sources, saccharides such as glucose, fructose, maltose, saccharose, glycerine, starch, bran, black molasses waste, and the like, and as nitrogen sources, organic nitrogen compounds such as peptone, meat extract, yeast extract, corn steep liquor, soybean meal, rapeseed oil cake, various amino acids, amino sugars, and the like, and inorganic nitrogen compounds such as ammonium nitrate, ammonium chloride, sodium nitrate and the like, can be used. And further it is preferable to add a trace amount of inorganic metal salts, vitamins, growth promoting factors, and the like.

Concentration of cholic acid in the culture medium, though not specifically restricted, is in the range of 1 to 500 g/l preferably 40 to 300 g/l as regards the yield of 12-keto-cholic acid and cultivation conditions.

Cultivation of the present invention may be performed in aerobic atmosphere, under, for example, ventilated agitation or reciprocal shaking. Cultivation conditions are usually set at 20° to 40° C. of the temperature, 7 to 11 of pH, and for 1 to 6 days of time.

A method for obtaining targeted 12-keto-cholic acid out of above media is as follows: at first, bacteria and unnecessary components in the culture media are removed by means of filtration, centrifugal separation, etc., and to the obtained filtrate or supernatant liquid, hydrochloric acid or sulfuric acid is added to make the filtrate or supernatant liquid acid. By this operation, 12-keto-cholic acid precipitates in the high yield. Then the precipitate is filtered, and after recrystallization, high purity 12-keto-cholic acid is obtained.

12-keto-cholic acid obtained according to the present invention may be easily converted by Wolff-Kishner reduction into chenodeoxycholic acid useful for gallstone solubilizing agent.

The present invention will be further explained with reference to the following examples, but it is understood that the examples are not meant to restrict the range of the present invention.

In each examples, the identification of the products is carried out by means of thin layer chromatography or high performance liquid chromatography under the condition as follows:

(1) Thin layer chromatography
  Carrier: Kieselgel 60 (0.25 mm thickness, Merk), Development
  Solution: benzene/isopropanol/acetic acid (40/10/1 volume ratio)
  Color change test: spraying phosphomolybdic acid—sulfuric acid reagent (dissolving 1 g of phosphomolybdic acid in 20 ml of methanol, and adding thereto 1 ml of concentrated sulfuric acid), and heating till a bile acid spot turns to deep blue.

(2) High performance liquid chromatography
  Column: INERTOSIL ODS column (column size 4.6$\phi$×250 mm, GL science)
  Mobile phase: methanol/refined water/phosphoric acid (70/30/0.02M weight ratio)
  Flow rate: 1.0 ml/min.
  Detector: RI

EXAMPLE 1

Bacillus sp. TTUR 2-M4-124 (FERM 3394) was cultivated according to the method as follows:

10 g of glucose, 5 g of peptone, 5 g of yeast extract, 1 g of dipotassium hydrogen phosphate and 0.2 g of magnesiumsulfate-7hydrates were dissolved in 500 ml of refined water, and separately 50 g of cholic acid, 5 g of sodium hydroxide and 10 g of sodium carbonate were dissolved in 500 g of refined water, and the two solutions were sterilized at the temperature of 121° C. for 15 minutes. After cooling, the two solutions were mixed, and the mixture was used for a culture medium (pH10).

Bacillus sp. TTUR 2-M4-124 (FERM 3394) was cultivated under shaking at the temperature of 30° C. for 20 hours in a test tube containing 20 ml of the culture medium of above composition except cholic acid and sodium hydroxide were excluded, in this manner a bacterium solution was prepared.

20ml of above culture medium was placed into a test tube(30$\phi$×190 mm), and 0.1 ml of said bacterium solution was aseptically inoculated therein, and the bacterium was cultivated under shaking at 30° C. for 3 days.

After this cultivation, the bacterium was removed by centrifugation, 12-keto-cholic acid and unconverted cholic acid were precipitated by adding diluted sulfuric acid to the supernatant liquid formed by said separating procedure and making said supernatant liquid acid. Then precipitate formed was collected, and after drying 0.999 g of white powder was obtained. A part of said powder was taken, and the ratio of cholic acid and 12-keto-cholic acid in the product was analyzed by means of high performance liquid chromatography, and the results were cholic acid 1.7%, 12-keto-cholic acid 98.3% ( recovery rate: 99.9% ). Pure 12-keto-cholic acid was obtained by recrystallization of the mixture in methanol solution.

EXAMPLE 2

The procedure of Example 1 was proceeded except that the bacterium was replaced by Bacillus sp. TTUR 2-M4-336 (FERM 3397), the ratio in the product was cholic acid 1.8%, 12-keto-cholic acid 98.2% ( recovery rate: 99.9% ).

EXAMPLE 3

The procedure of Example 1 was proceeded except that glucose was excluded from the culture medium (pH10), the production ratio was cholic acid 1.9%, 12-keto-cholic acid 98.1%.

EXAMPLE 4

The procedure of Example 2 was proceeded except that glucose was excluded from the culture medium (pH10), the ratio in the product was cholic acid 0%, 12-keto-cholic acid 100%.

EXAMPLE 5

10 g of soybean protein (ESUSAN-MEAT; trade name; AJINOMOTO Inc. ), 1 g of dipotassium hydrogen phosphate and 0.2 g of magnesium sulfate 7hydrates were dissolved in 500 ml of refined water, and 50 g of cholic acid, 5 g of sodium hydroxide and 2 g of sodium carbonate were dissolved in 500 ml of refined water, then both solutions were sterilized at the temperature of 121° C. for 15 minutes. After cooling, two solutions were mixed and the mixture was used for a culture medium (pH10.2). Thereafter, the same procedure as Example 1 was proceeded and 12-keto-cholic acid was obtained. The ratio in the product was cholic acid 0.5% and 12-keto-cholic acid 99.5%.

EXAMPLE 6

The procedure of Example 5 was proceeded except that the bacterium was replaced by Bacillus sp. TTUR 2-M4-336. The ratio in the product was cholic acid 1.2%, 12-keto-cholic acid 98.8%.

EXAMPLE 7

The procedure of Example 5 was proceeded except that dipotassium hydrogen phosphate and magnesium-sulfate 7hydrates were excluded from the medium and the amount of sodium carbonate was changed to 3g (pH10.3). The ratio in the product was cholic acid 0%, 12-keto-cholic acid 100%.

EXAMPLE 8

The procedure of Example 7 was proceeded except that the bacterium was replaced by Bacillus sp. TTUR 2-M4-336. The ratio in the product was 0.7%, 12-keto-cholic acid 99.3%.

EXAMPLE 9

10g of soybean protein (ESUSAN MEAT), 1 g of yeast extract, 1 g of dipotassium hydrogen phosphate and 0.2 g of magnesium sulfate 7hydrates were dissolved in 500 ml of refined water, and 50 g of cholic acid, 5 g of sodium hydroxide and 4 g of sodium carbonate were dissolved in 500 ml of refined water, then both solutions were sterilized at the temperature of 121° C. for 15 minutes. After cooling, two solutions were mixed and the mixture was used for a culture medium (pH10.2). Then, the procedure of Example 5 was proceeded except that the bacterium was replaced by Bacillus sp. TTUR 2-M4-336. The ratio in the product was cholic acid 0.1% and 12-keto-cholic acid 99.9%.

EXAMPLE 10

The procedure of Example 9 was proceeded except that soybean protein (ESUSAN-MEAT) was excluded from the medium and, instead, 20 g of corn steep liquor was added to the medium, and the amount of sodium carbonate was changed to 12 g (pH9.8). The ratio in the product was cholic acid 0.1%, 12-keto-cholic acid 99.9%.

EXAMPLE 11

The procedure of Example 5 was proceeded except that soybean protein (ESUSAN-MEAT) was excluded from the culture medium, instead, 10 g of soybean protein (AJIPRON E3; trade name: AJINOMOTO Inc. ) was added, and the amount of sodium carbonate was changed to 2 g (pH10.0), and cultivation time was shortened to two days. The ratio in the product was cholic acid 0.2%, 12-keto-cholic acid 99.8%.

EXAMPLE 12

The procedure of Example 11 was proceeded except that the bacterium was replaced by Bacillus sp. TTUR 2-M4-336 and cultivation time was extended to 3 days. The ratio in the product was cholic acid 0.4%, 12-keto-cholic acid 99.6%.

EXAMPLE 13

5g of yeast extract, 1 g of dipotassium hydrogen phosphate and 0.2 g of magnesiumsulfate 7hydrate were dissolved in 500 ml of refined water, and 50 g of cholic acid, 5 g of sodium hydroxide and 4 g of sodium carbonate were dissolved in 500 ml of refined water, then both solutions were sterilized at the temperature of 121° C. for 15 minutes. After cooling, two solutions were mixed and the mixture was used for a culture medium (pH9.7). Thereafter, the same procedure as Example 1 was proceeded. The ratio in the product was cholic acid 0.4% and 12-keto-cholic acid 99.6%.

EXAMPLE 14

The procedure of Example 13 was proceeded except that the bacterium was replaced by Bacillus sp. TTUR 2-M4-336. The ratio in the product was cholic acid 0.1%, 12-keto-cholic acid 99.9%.

EXAMPLE 15

The procedure of Example 14 was proceeded except that yeast extract was excluded from the culture medium and instead 5 g of soybean peptide (D-4; trade name: FUJISEIYU Inc. ) was added to the medium (pH9.8). The ratio in the product was cholic acid 0.8%, 12-keto-cholic acid 99.2%.

EXAMPLE 16

The procedure of Example 13 was proceeded except that yeast extract was excluded from the culture medium, and instead, 5 g of soybean peptide (D-2; trade name: FUJISEIYU Inc.) was added and the amount of sodium carbonate was changed to 2 g (pH of the medium is 9.2). The ratio in the product was cholic acid 0.1%, 12-keto-cholic acid 99.9%.

EXAMPLE 17

10 g of glucose, 5 g of peptone, 5 g of yeast extract, 1 g of dipotassium hydrogen phosphoric acid and 0.2 g of magnesiumsulfate 7hydrates were dissolved in 500 ml of refined water. And 100 g of cholic acid, 10 g of sodium hydroxide and 10 g of sodium carbonate were dissolved in 500 g of refined water. Then both solutions were sterilized at the temperature of 121° C. for 15 minutes. After cooling, the two solutions were mixed and the mixture was used for a culture medium (pH10).

Bacillus sp. TTUR 2-M4-124 was cultivated under shaking at the temperature of 30° C. for 24 hours in a test tube containing 20 ml of the culture medium of the above composition, and a bacterium solution was prepared. 20 ml of said culture medium was placed into a test tube (30$\phi$×190 mm), and 0.2 ml of said bacterium solution was aseptically inoculated therein, and the bacterium in the test tube was cultivated under shaking at 30° C. for 4 days.

The same procedure as Example 1 was proceeded thereafter and 12-keto-cholic acid was obtained. The ratio in the product was cholic acid 3.3% and 12-keto-cholic acid 96.7%.

EXAMPLE 18

The procedure of Example 17 was proceeded except that the bacterium was replaced by Bacillus sp. TTUR 2-M4-336. The ratio in the product was cholic acid 2.7%, 12-keto-cholic acid 97.3%.

EXAMPLE 19

10 g of glucose, 5 g of peptone, 5 g of yeast extract, 1 g of dipotassium hydrogen phosphate and 0.2 g of magnesium sulfate 7hydrates were dissolved in 500 ml of refined water, and 50 g of cholic acid, 5 g of sodium hydroxide and 10 g of sodium carbonate were dissolved in 500 g of refined water, then both solutions were sterilized at the temperature of 121° C. for 15 minutes.

After cooling, the two solutions were mixed and the mixture was used for a medium (pH10).

Bacillus sp. TTUR 2-M4-124 was cultivated under shaking at the temperature of 30° C. for 24 hours in a test tube containing 20 ml of above culture medium, and bacterium solution was prepared. 20 ml of above culture medium was placed into a test tube(30φ×190 mm), and 0.2 ml of the bacterium solution was aseptically inoculated therein, and the bacterium in the test tube was cultivated under shaking at 30° C. for 2 days. The same procedure as the example 1 was proceeded thereafter and obtained 12-keto-cholic acid. The production ratio was cholic acid 0.7% and 12-keto-cholic acid 99.3%.

EXAMPLE 20

The procedure of Example 19 was proceeded except that the bacterium was replaced by Bacillus sp. TTUR 2-M4-336. The production ratio was cholic acid 0.8%, 12-keto-cholic acid 99.2%.

EXAMPLE 21

10 g of glucose, 5 g of peptone, 5 g of yeast extract, 1 g of dipotassium hydrogen phosphate and 0.2 g of magnesium sulfate 7hydrates were dissolved in 500 ml of refined water. 150 g of cholic acid, 15 g of sodium hydroxide and 10 g of sodium carbonate were dissolved in 500 g of refined water. And the two solutions were sterilized at the temperature of 121° C. for 15 minutes. After cooling, the solutions were mixed and the mixture was used for a culture medium (pH10).

Bacillus sp. TTUR 2-M4-124 was cultivated under shaking at the temperature of 30° C. for 24 hours in a test tube containing 20 ml of above culture medium, thus bacterium solution was prepared. 20 ml of above culture medium was placed into a test tube(30φ×190 mm), 0.2 ml of said bacterium solution was aseptically inoculated therein, and the bacterium in the test tube was cultivated under shaking at 30° C. for 6 days. Thereafter, the same procedure as Example 1 was proceeded and 12-keto-cholic acid was obtained. The production ratio was cholic acid 17.3% and 12-keto-cholic acid 82.7%.

EXAMPLE 22

The procedure of Example 21 was proceeded except that the bacterium was replaced by Bacillus sp. TTUR 2-M4-336. The ratio in the product was cholic acid 15.2%, 12-keto-cholic acid 84.8%.

EXAMPLE 23

20 g of glucose, 10 g of peptone, 10 g of yeast extract, 2 g of dipotassium hydrogen phosphate and 0.4 g of magnesium sulfate 7hydrates were dissolved in 1000 ml of refined water. 100 g of cholic acid, 10 g of sodium hydroxide and 20 g of sodium carbonate were dissolved in 1000 g of refined water. And the two solutions were sterilized at the temperature of 121°C. for 15 minutes. After cooling, the solutions were mixed in a desktype jar fermenter apparatus (5l size), and the mixture was used for a culture medium (pH10).

Bacillus sp. TTUR 2-M4-124 was cultivated under shaking at the temperature of 30° C. for 24 hours in a test tube containing 20 ml of the culture medium of above composition except cholic acid and sodium hydroxide were excluded, thus bacterium solution was prepared. 20 ml of above culture medium was placed into a test tube(30φ×190 mm), 40 ml of said bacterium solution was aseptically inoculated therein, and the bacterium in the jar fermenter was cultivated under agitation (300 rpm) at the aeration rate 2l/min. at 30° C. for three days.

After above cultivation, the bacteria was removed by means of centrifugal separation, and by adding diluted sulfuric acid to the supernatant liquid formed by said centrifugation, the pH was controlled at 2.5, 12-keto-cholic acid and unconverted cholic acid were precipitated. The precipitate was filtered, washed with water, and crystal was obtained and, after drying at the temperature of 50° C., 99.2g of white powder was obtained. A part of said powder was taken for characterization, and the ratio of cholic acid and 12-keto-cholic acid in the product was analyzed by means of high performance liquid chromatography, and the results were cholic acid 1.1%, 12-keto-cholic acid 98.9% (recovery rate: 99.2%).

EXAMPLE 24

The procedure of Example 23 was proceeded except that the bacterium was replaced by Bacillus sp. TTUR 2-M4-336. The ratio in the product was cholic acid 0.4%, 12-keto-cholic acid 99.6% ( recovery rate: 98.9% ).

EXAMPLE 25

20 g of soybean protein (ESUSAN MEAT) was dissolved in 1000 ml of refined water, and 100 g of cholic acid, 10 g of sodium hydroxide and 6 g of sodium carbonate were dissolved in 1000 g of refined water, and the two solutions were sterilized at the temperature of 121° C. for 15 minutes. After cooling, the solutions were mixed in a desktype jar fermenter apparatus (5l size), and the mixture was used for a culture medium (pH10.4).

Bacillus sp. TTUR 2-M4-336 was cultivated under shaking at the temperature of 30° C. for 24 hours in a test tube containing 20 ml of the culture medium of above composition except cholic acid and sodium hydroxide were excluded, thus a bacterium solution was prepared. 20 ml of above culture medium was placed into a test tube(30φ×190 mm), 40 ml of said bacterium solution was aseptically inoculated therein, and the bacterium in the test tube was cultivated under agitation (300 rpm) at the aeration rate 2l/min. at 30° C. for three days. A trace amount of antifoaming agent (EINOL; trade name; BIOTT Co. LTD) was added during this operation. And thereafter, the same procedure as Example 23 was proceeded and 12-keto-cholic acid was obtained. The ratio in the product was cholic acid 0.7%, 12-keto-cholic acid 99.3% ( recovery rate: 99.2% ).

EXAMPLE 26

20 g of soybean protein (AJIPRON E3), 2 g of dipotassium hydrogen phosphate and 0.4 g of magnesium sulfate 7hydrates were dissolved in 1000 ml of refined water, and 100 g of cholic acid, 10 g of sodium hydroxide and 5 g of sodium carbonate were dissolved in 1000 ml of refined water, then both solutions were sterilized at the temperature of 121° C. for 15 minutes. After cooling, the two solutions were mixed in a desktype jar fermenter apparatus (5l size), and the mixture was used for a culture medium (pH10.5). Thereafter, the procedure of Example 23 was proceeded except that the cultivation time was changed to two days. The ratio in the product was cholic acid 0.4% and 12-keto-cholic acid 99.6% (recovery rate: 99.8% ).

EXAMPLE 27

The procedure of Example 26 was proceeded except that the bacterium was replaced by Bacillus sp. TTUR 2-M4-336, that cultivation time was changed to three days and that a trace amount of antifoaming agent (EINOL) was added during the cultivation. The ratio in the product was cholic acid 0.4%, 12-keto-cholic acid 99.6% ( recovery rate: 99.2%).

EXAMPLE 28

10 g of soybean protein (AJIPRON E3), 1 g of yeast extract, 2 g of dipotassium hydrogen phosphate and 0.4 g of magnesium sulfate 7hydrates were dissolved in 1000 ml of refined water, and 100 g of cholic acid, 10 g of sodium hydroxide and 6 g of sodium carbonate were dissolved in 1000 ml of refined water, then both solutions were sterilized at the temperature of 121° C. for 15 minutes. After cooling, two solutions were mixed in a desktype jar fermenter apparatus (5l size), and the mixture was used for a culture medium (pH10.7). Thereafter, the same procedure as Example 26 was proceeded. The ratio in the product was cholic acid 0.6% and 12-ketocholic acid 99.4% (recovery rate 98.9%).

EXAMPLE 29

The procedure of Example 28 was proceeded except that the bacterium was replaced by Bacillus sp. TTUR 2-M4-336, that cultivation time was changed to three days and that a trace amount of antifoaming agent (EINOL) was added during the cultivation. The ratio in the product was cholic acid 0.6%, 12-keto-cholic acid 99.4% ( recovery rate: 99.4% ).

EXAMPLE 30

10 g of soybean protein (AJIPRON E3), 1 g of yeast extract, 2 g of dipotassium hydrogen phosphate and 0.4 g of magnesium sulfate. 7hydrates were dissolved in 1000 ml of refined water, and 100 g of cholic acid, 10 g of sodium hydroxide and 5 g of sodium carbonate were dissolved in 1000 ml of refined water, and without sterilization, two solutions were mixed in a desktype jar fermenter apparatus(5l size), and the mixture was used for a culture medium (pH0.4).

Bacillus sp. TTUR 2-M4-124 was cultivated under shaking at the temperature of 30° C. for 20 hours in a test tube containing 20 ml of above culture medium and thus a bacterium solution was prepared. 40 ml of said bacterium solution was aseptically inoculated therein, and the bacterium in the jar fermenter was cultivated under agitation (300 rpm) at the aeration rate 2l/min. at 30° C. for three days. And thereafter, the same procedure as Example 23 was proceeded. The ratio in the product was cholic acid 0%, 12-keto-cholic acid 100% ( recovery rate: 99.1% ).

EXAMPLE 31

The procedure of Example 30 was proceeded except that the bacterium was replaced by Bacillus sp. TTUR 2-M4-336. The ratio in the product was cholic acid 1.5%, 12-keto-cholic acid 98.5% ( recovery: rate 98.8% ).

We claim:

1. A biologically pure culture of Bacillus Sp. FERM BP-3394.

2. A biologically pure culture of Bacillus sp. FERM BP-3397.

3. Process for producing 3-alpha, 7-alpha-dihydroxy-12-keto-5-beta-cholanic acid from cholic acid, which comprises cultivating an alkalophilic microorganism belonging to the genus Bacillus in a nutrient medium containing cholic acid under aerobic conditions at alkaline pH, and recovering the thereby produced 3-alpha, 7-alpha-dihydroxy-12-keto-5-beta-cholanic acid wherein said microorganism is selected from the group consisting of Bacillus sp. FERM BP-3394 and Bacillus sp. FERM BP-3397.

4. Process of claim 3 wherein the pH of the nutrient medium is an alkaline pH up to about 11, and the cholic acid is present in a concentration of about 1 to 500 g/L.

* * * * *